United States Patent [19]
Kriesel et al.

[11] Patent Number: 5,314,405
[45] Date of Patent: May 24, 1994

[54] LIQUID DELIVERY APPARATUS

[75] Inventors: Marshall S. Kriesel, Saint Paul; Thomas N. Thompson, Richfield, both of Minn.

[73] Assignee: Science Incorporated, Bloomington, Minn.

[21] Appl. No.: 870,403

[22] Filed: Apr. 17, 1992

[51] Int. Cl.⁵ .............................................. A61M 5/00
[52] U.S. Cl. .................................................. 604/8; 604/9
[58] Field of Search .................... 604/8, 9, 10, 247; 137/504, 508, 510, 849

[56] References Cited

U.S. PATENT DOCUMENTS

| | | |
|---|---|---|
| 3,998,378 | 12/1976 | Vetten . |
| 4,239,150 | 12/1980 | Schadowski et al. . |
| 4,254,693 | 3/1981 | Schadowski et al. . |
| 4,287,247 | 9/1981 | Reil et al. . |
| 4,681,560 | 7/1987 | Schulte ............................ 604/8 |
| 4,688,595 | 8/1987 | Srebnik et al. . |
| 4,761,158 | 8/1988 | Schulte ............................ 604/8 |
| 4,781,672 | 11/1988 | Hooven ............................ 604/9 |
| 4,816,016 | 3/1989 | Schulte ............................ 604/8 |
| 4,826,500 | 5/1989 | Rantsola . |
| 4,979,937 | 12/1990 | Khorasani ........................ 604/8 |
| 4,983,431 | 1/1991 | Gibbons et al. : |
| 4,995,856 | 2/1991 | Heindl ............................. 604/8 |
| 5,084,015 | 1/1992 | Moriuchi ........................ 604/9 |

*Primary Examiner*—Michael A. Brown
*Attorney, Agent, or Firm*—James E. Brunton

[57] ABSTRACT

A self-contained system for the enteral delivery of a nutrient solution from an aseptic package without the intermediate step of emptying the package contents into a traditional flexible bag solution container for delivery by parastalic pump, gravity means or the like.

The system of the invention uniquely includes a novel, distendable membrane stored energy source which functions to automatically deliver on demand the premixed solution contained within the package to the patient at a precisely controlled rate.

20 Claims, 7 Drawing Sheets

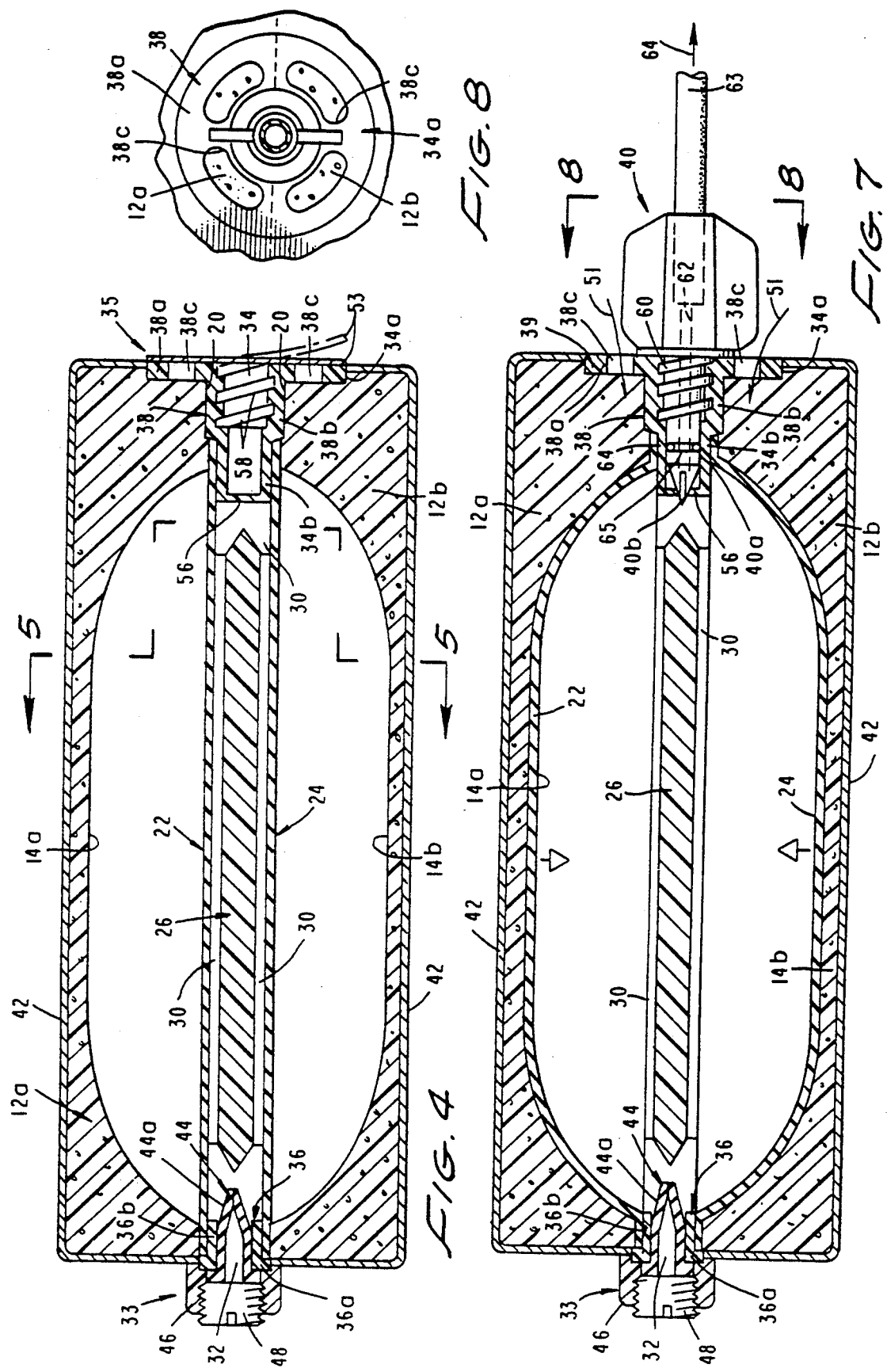

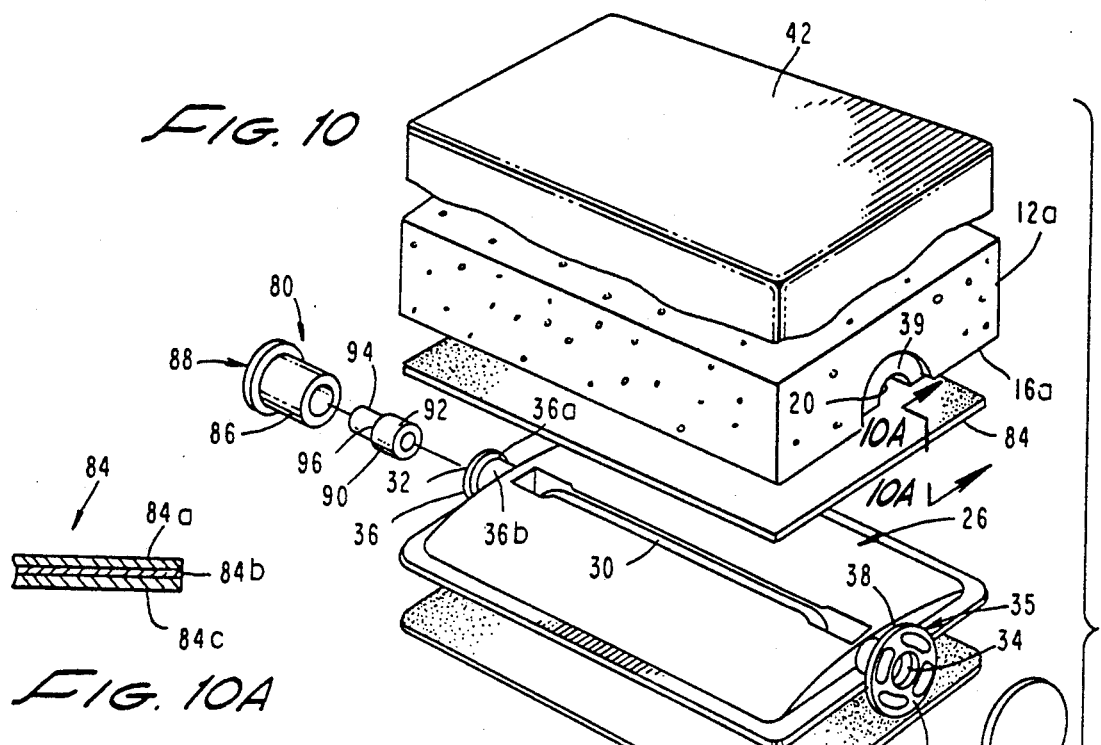
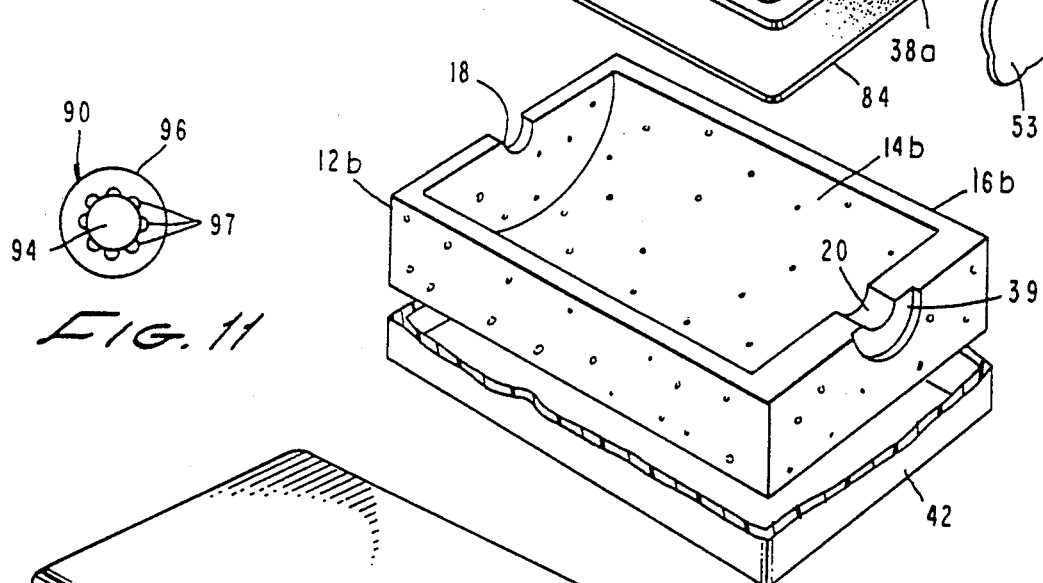
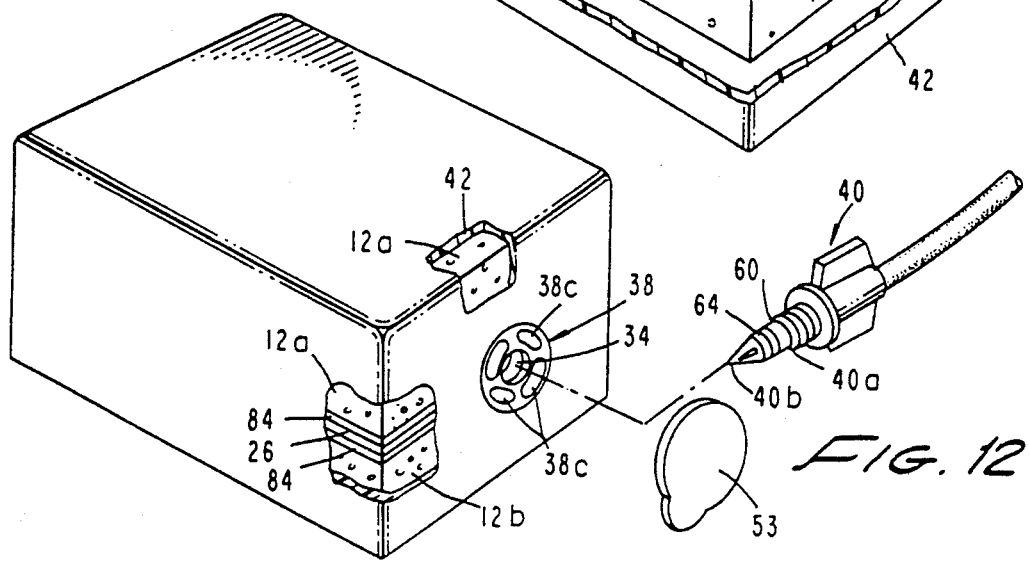

LIQUID DELIVERY APPARATUS

BACKGROUND OF THE INVENTION

1. Field of the Invention

The present invention relates generally to liquid delivery systems. More particularly, the invention concerns an apparatus for enteral feeding applications.

2. Discussion of the Invention

When patients are comatose, or for some reason are unable to take nourishment by mouth, enteral feeding becomes necessary. Enteral nutrition, or tube feeding, is typically accomplished by nasogastric administration or by direct delivery of liquids to the stomach via a surgically implanted feeding tube. Parastalic pumps are currently used for nasogastric feeding when gravity flow from an elevated container is insufficient to instill flow or when an exact amount of regulated feeding is necessary. Such devices are cumbersome to use and at times have proven unreliable.

The apparatus of the present invention overcomes the drawbacks of prior art enteral feeding systems by providing a self-contained apparatus which includes an internal energy source that automatically expels prepackaged nutritional liquids from a sealed aseptic container at a desired uniform rate.

Aseptic packaging is, of course, not new. Such packaging is being used more and more in the food industry for packaging fruit juice, milk products and the like. Additionally, some use of aseptic packaging has been made in the medical field for packaging medical solutions.

When the packaged, aseptically filled liquid is a food product, such as fruit juice, the sealed package is typically punctured at a specific site location and the juice is withdrawn through a straw. When the packaged liquid is a medical solution, the package is typically opened, mixed with other components when required and emptied into a traditional, wide-mouth flexible bag solution container for enteral delivery by conventional gravity means and parastalic pump. However, in U.S. Pat. No. 4,826,500 issued to Rantsola, a system for the enteral delivery of a medical solution directly from an aseptic container is there described. In accordance with the methods of the Rantsola patent, the solution is passed from a container through an elongated giving set and metering system into a nasal tube. The container is an aseptic carton having penetrable side walls, with the giving set being provided with a fitting having a fluid passage extending therethrough. The fitting terminates at a carton cooperating portion which includes a first portion for penetrating the carton side walls to form an orifice therein, the orifice establishing fluid communication between the carton interior and the fitting fluid passage, and a second portion for engaging the carton side wall to maintain cooperation between the carton and fitting.

In U.S. Pat. No. 4,688,595, issued to Srebnik, et al, there is described an enteral nutrition delivery system which comprises an integral molded plastic base which includes a first platform to which is secured an infusion pump and a second platform having a recess in which is secured a specially designed bottle containing nutritional fluid to be fed to a patient. A tubing net-work is included for interconnecting the pump, bottle and the patient.

Neither Rantsola nor Srebnik, et al disclose or remotely suggest the novel apparatus of the present invention, which comprises a prefilled, self-contained system, including a unique stored energy source disposed within an aseptic package for delivering the nutritional liquid at a controlled, uniform rate.

Through use of the novel apparatus of the present invention, the disadvantageous current practice of preparing the dry nutrient composition and mixing it with sterile water at the point of use is avoided. The current practice of preparing the dry nutrient composition and mixing with sterile water at point of use has many obvious disadvantages. Historically, the use of this two-step method of treatment preparation has, in part, been driven by the problems resulting from combined solution sterilization, including chemical reactivity of certain nutrient materials under autoclave conditions because of the flexible bag. Prior art practices also typically employ intermittent feeding of the patient. Recent clinical practice now favors continuous feeding rather than intermittent feeding in most cases. In accordance with the present invention, certain drugs, minerals, nutrients and the like are aseptically sealed in a multibarrier layer, oxygen impermeable, moisture-proof, microorganism-impermeable aseptic dispenser for automatic, on-demand continuous delivery to the patient without the required use of a parastalic pump or external energy sources of any kind.

SUMMARY OF THE INVENTION

It is an object of the present invention to provide a self-contained system for the enteral delivery of a nutrient solution from an aseptic package without the intermediate step of emptying the package into a traditional flexible bag solution container for delivery by parastalic pump, gravity means or the like.

More particularly, it is an object of the invention to provide a system of the aforementioned character in which an integral, inherently sterile, flat film energy source is contained within the aseptic package for automatically delivering on demand the premixed solution contained within the package to the patient at a precisely controlled rate.

Another object of the invention is to provide an aseptic carton having a non-permeable oxygen barrier with a penetrating portion for sealable penetration by a fitting having a fluid passageway therethrough in communication with a giving set.

Another object of the invention is to provide a carton as described in the preceding paragraph in which provision is made for ingress of make-up air so that an even outflow of solution to the patient is precisely maintained.

Another object of the invention is to provide a carton which utilizes a paper-board barrier laminated structure that maintains an isolated gas environment within the container.

Still another object of the invention is to provide a system of the class described in which the aseptic container and flat film integral energy source, or elastomeric membrane, can be economically mass produced at low cost to permit the discard of the assembly after use.

BRIEF DESCRIPTION OF THE DRAWINGS

FIG. 4 is a cross-sectional view taken along lines 4—4 of FIG. 3.

FIG. 7 is a cross-sectional view similar to FIG. 4 but illustrating the appearance of the apparatus when filled with fluid.

FIG. 8 is a fragmentary view taken along lines 8—8 of FIG. 7.

FIG. 10 is a generally perspective exploded view of an alternate form of the apparatus of the invention.

FIG. 10A is a cross-sectional view taken along lines 10A—10A of FIG. 10.

FIG. 11 is a cross-sectional view of the check valve assembly of FIG. 10.

FIG. 12 is a generally perspective view of the apparatus of FIG. 10 partly broken away to show internal construction and exploded to show the manner of interconnection of the delivery spike.

DESCRIPTION OF THE INVENTION

Figure 1:
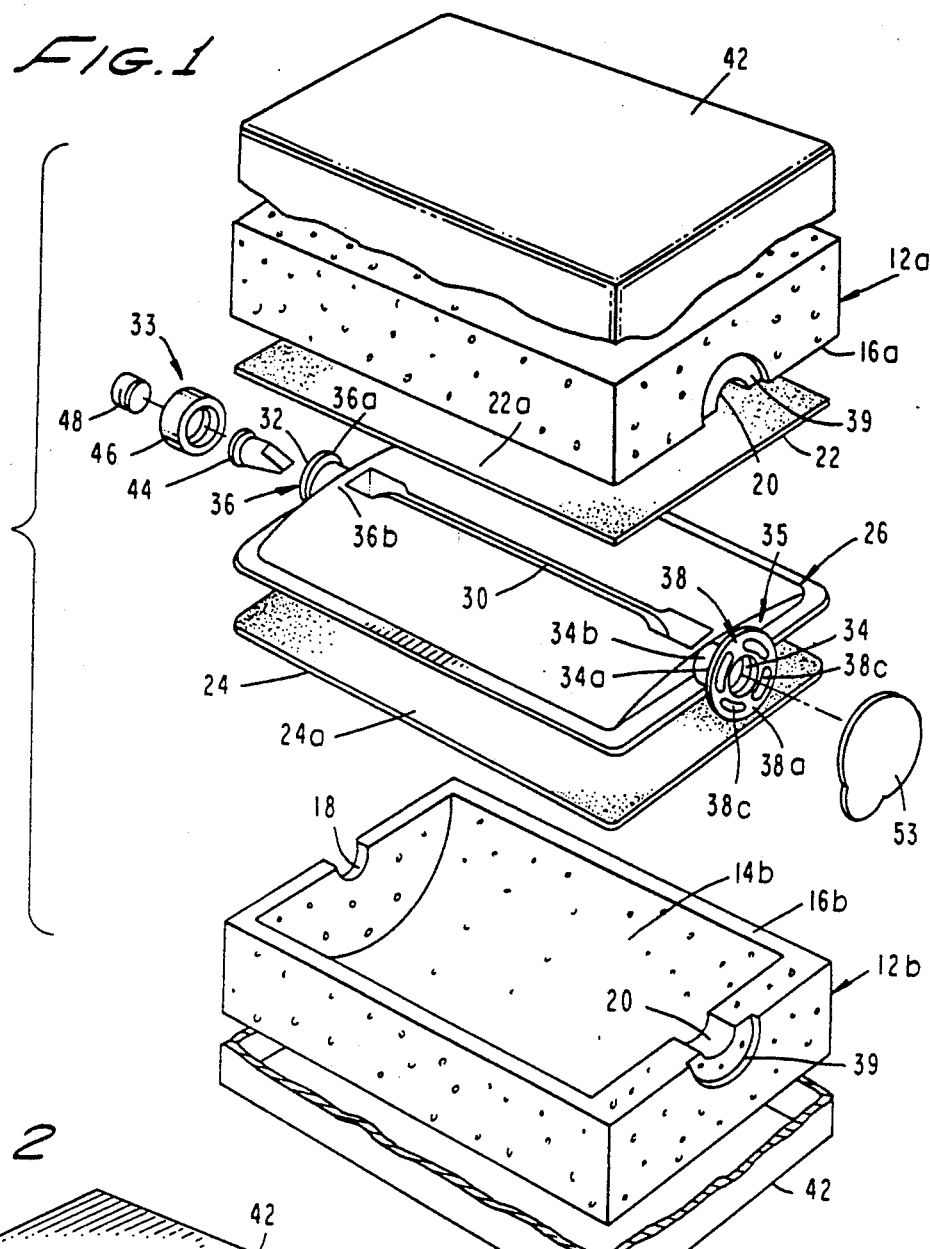
FIG. 1 is a generally perspective exploded view of the nutrient delivery apparatus of the present invention.
Figure 2:
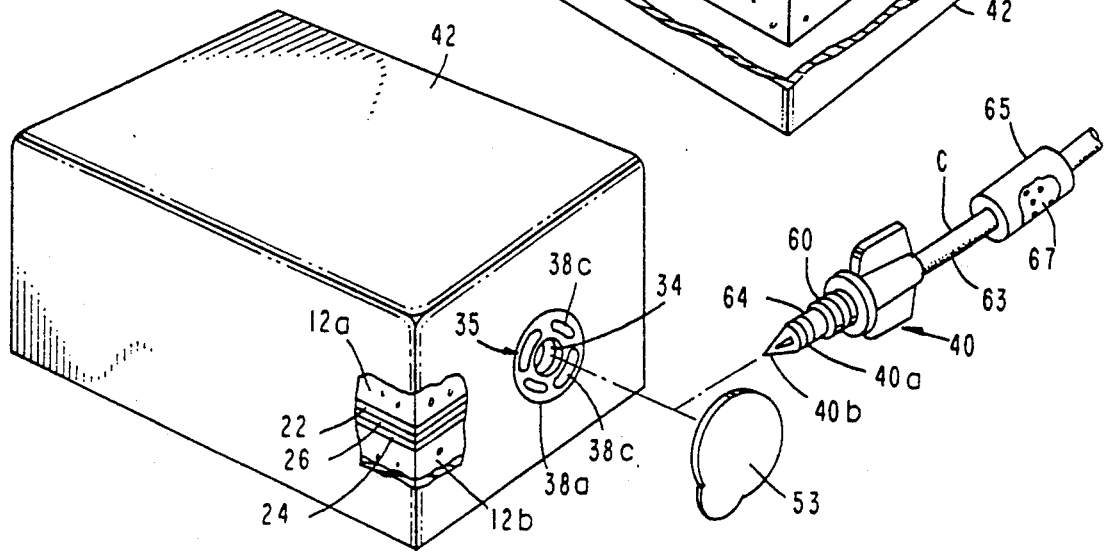
FIG. 2 is a perspective view of the apparatus partly broken away to show internal construction and exploded to show the manner of interconnection of the liquid delivery spike.
Figure 3:
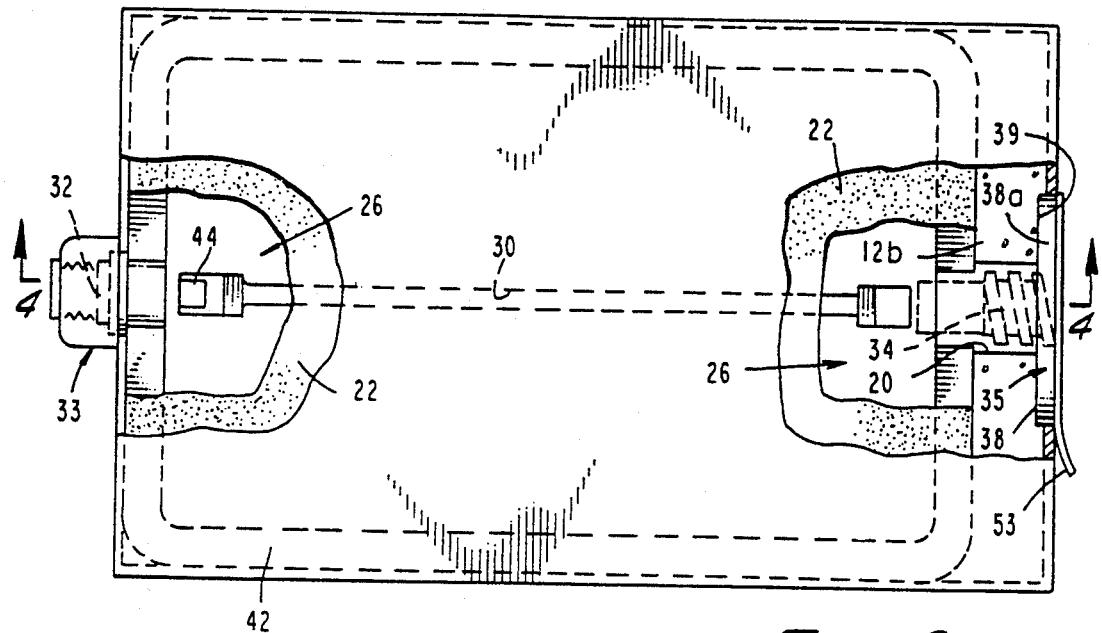
FIG. 3 is a top-plan view of the device partly broken away to show internal construction.

Referring to the drawings and particularly to FIGS. 1, 2 and 3, the liquid delivery apparatus of the present invention comprises a body made up of cooperating first and second portions 12a and 12b respectively. As can best be seen by referring to FIG. 5, each body portion 12a and 12b includes internal walls defining cavities 14a and 14b respectively with each cavity being circumscribed by an edge 16a and 16b respectively. Each body portion is also provided at either end with semi-circular shaped, indexable openings generally designated by the numerals 18 and 20.

A first distendable membrane 22 is provided with an edge portion 22a which is disposed in engagement with edge portion 16a of first body portion 12a. A second distendable membrane 24 having an edge portion 24a is disposed in engagement with edge portion 16b of second body portion 12b. Each of the distendable membranes 22 and 24, the unique character of which will presently be described, includes a central portion 22b and 24b respectively which spans the cavity of the body portion with which the membrane is associated (FIG. 5).

Disposed between distendable membranes 22 and 24 is a rigid support, or ullage member 26. Support member 26, which can be constructed from any suitable plastic such as polypropylene, polystyrene, polyethylene, or polycarbonate, is provided with a longitudinally extending fluid passageway 30 which is in communication at one end with a fluid inlet port 32 of an inlet port assembly 33 and is in communication at its opposite end with a fluid outlet port 34 of an outlet port assembly 35. Fluid inlet port assembly 33 includes an inlet adapter 36 having a flange portion 36a and a neck portion 36b which is closely received within apertures 18 provided in body portions 12a and 12b. Similarly, outlet port 34 includes a flange portion 34a and a neck portion 34b which portion is closely received within apertures 20 provided in body portions 12a and 12b. It is to be noted that body portions 12a and 12b are also provided with semicircular shaped recessed portions 39 which are adapted to closely receive flange portion 38a of outlet port adapter 38 which in this form of the invention comprises a port of the vent means for permitting the flow of gases between atmosphere and the interior of the liquid delivery apparatus.

Also comprising a part of the liquid delivery apparatus of the form of the invention shown in the drawings is a fluid delivery means which is in communication with the fluid outlet port of the apparatus. In a manner presently to be described, the fluid delivery means functions to deliver fluid to the patient. This fluid delivery means is shown in FIG. 2 as comprising a delivery spike assembly 40, which is adapted to cooperate with the fluid outlet port assembly 35.

Figure 5:
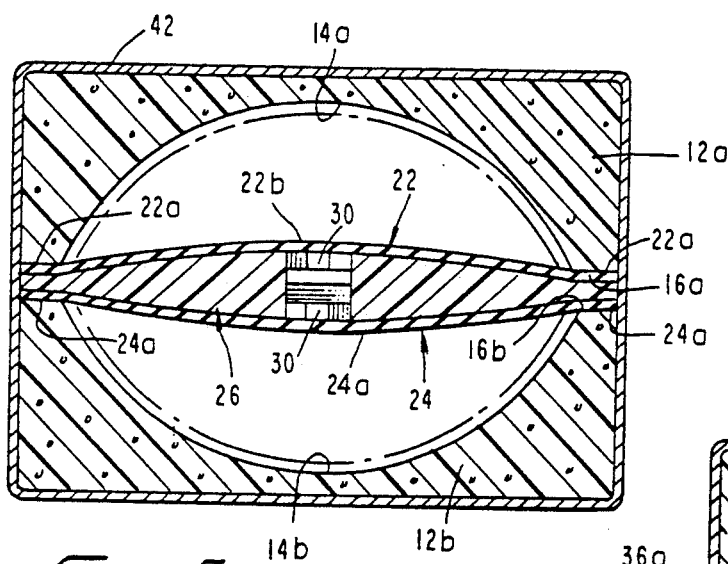
FIG. 5 is a cross-sectional view taken along lines 5—5 of FIG. 4.
Figure 9:
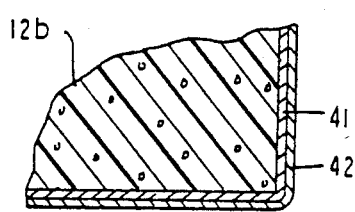
FIG. 9 is a fragmentary cross-sectional view illustrating one form of the multi-film barrier construction of the device.

As best seen by referring to FIGS. 2 and 5, body portions 12a and 12b are encapsulated by oxygen non-permeable encapsulating barrier means shown here as thin layers of material 41 and 42 sealably surrounding body portions 12a and 12b (FIG. 9). The character of this sealing material and the manner in which it is applied will be discussed hereinafter.

Receivable within fluid filling inlet adapter 36 is a check valve assembly comprising a duckbill-type check valve 44 of conventional construction which is held in position within neck portion 36b by an internally threaded retainer ring 46 which is received over flange portion 36a. A threaded closure plug 48 is threadably received within retainer ring 46 in the manner best seen in FIG. 4. Duckbill valve 44 includes a yieldably deformable "bill" 44a which functions in the traditional manner illustrated in FIGS. 6 and 7, permitting fluid to flow inwardly in the direction of the arrows designated by the numerals 50 in FIG. 6, but blocking fluid flow in the opposite direction in the manner shown in FIG. 7. It is to be understood that various types of check valves of a character well known to those skilled in the art can be used in place of the duckbill valve 44.

Body portions, or structural support members 12a and 12b can be constructed of any suitable gas permeable, porous material such as Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. A suitable source of these materials is Porex Technologies of Fairburn, Ga. However, practice has shown that any porous plastic material including an open cell, porous sponge material which permits the free passage of gases therethrough is suitable. As described in the following paragraphs, to enable venting of gases from the fluid chamber, membranes 22 and 24 can also be constructed from a suitable gas permeable material.

In practice membranes 22 and 24 can be single layers or laminates and can be manufactured from several alternate materials including rubber, plastics and other thermo-plastic elastomers. These include latex, rubber polyisoprene, butyl rubber, nytrial rubber, other homopolymer, copolymers, mechanical poly blends and interpenetrating polymer networks. Examples of materials found particularly well suited for the construction of the high gas permeable membranes include silicon polymers which are castable into thin film membranes having high gas permeability. Depending upon the fluid to be dispensed from the apparatus, other materials of choice for fabricating the membranes include polyurethane-polysiloxane, copolymers, blends and IPNs (interpenetrating polymer network materials). In certain applications, low gas permeable membranes such as floro-silicons and floro-elastomers may be desirable. Manufacturers of materials suitable for use in the construction of the distendable membranes 22 and 24 include Dow Chemical, 3M Company, General Electric, Mobay Chemical, Shell Oil Corporation, DuPont, and Union Carbide Corporation.

The previously mentioned vent means of the invention is adapted to provide for make-up air during liquid delivery so that an even outflow of solution from the apparatus is obtained. To permit the flow of gases between atmosphere and the interior of the apparatus, flange 38a of outlet adapter 38 is provided with circumferentially spaced apertures 38c which permit free flow of air toward fluid chambers 14a and 14b in the manner shown by the arrows 51 in FIG. 7. In practice an oxygen impermeable sterile barrier patch 5 is removably affixed to flange 34 so as to cover apertures 38c.

By referring to FIG. 8, it can be seen that the encapsulating means, shown here as an outer barrier which surrounds the body portions 12a and 12b is perforated in the area of the apertures 38c provided in the flange 38. These apertures in the outer barrier permit air from atmosphere to flow into the porous body portions 12a and 12b in the manner shown by the arrows in FIG. 7 and designated by the numeral 51.

Turning to FIG. 9, the encapsulating means or outer barrier in the embodiment of the invention there shown comprises an outer paper wrap 42 covering an inner metalized wrap or encapsulation material 41. The outer barrier or encapsulating means can take several forms so long as it produces an oxygen impermeable, antimicrobial leak-free aseptic container. For example, the encapsulation means can comprise a barrier laminate structure which is made up of a plurality of specific high-strength polymer resin layers which effectively prevent formation of pin holes or cracking of oxygen barrier layers during package formation. One type of oxygen impermeable, leak-free container material is disclosed in U.S. Pat. No. 4,983,431 issued to Gibbons et al. Disclosures in this patent relating to leak-free packaging are also applicable to the encapsulation means of the aseptic package of the present invention. U.S. Pat. No. 3,998,378 issued to Vetten describes methods of fabricating a folding box having a liquid tight cemented bottom and improved stability. Techniques discussed in the Vetten patent can also be used in the construction of the outer barrier or encapsulating means of the present invention. To patents cited in Gibbons, et al. and Vetten are also pertinent to the construction of the encapsulation barrier of the present invention. Other pertinent prior art U.S. Pat. Nos. include 4,239,150 issued to Schadowski, et al., 4,254,693 issued to Shadowsski, et al., and 4,287,247 issued to Reil, et al. The teachings of these prior art patents and the patents cited therein are more than adequate to inform those skilled in the art of the various techniques and materials that can be used in fabricating the encapsulating means, including oxygen impermeable aseptic containers, of the invention.

Turning now to FIGS. 4 and 7, it is to be observed that outlet port 34 is initially closed by a frangible diaphragm 56 which form an integral part of the outlet adapter 38. It is also to be noted that neck 38b of outlet adapter 38 is internally threaded with threads 58 which are adapted to threadably receive external threads 60 provided on the delivery spike assembly 40. Delivery spike assembly 40 includes an outwardly extending, generally cylindrically shaped portion 40a that terminates in a sharp spike or point 40b. Point 40b is adapted to pierce frangible membrane 56 when the delivery spike is threadably connected with the outlet port assembly 34 in the manner illustrated in FIG. 7. An elastomeric 0 ring 64 is received within a groove 65 provided in cylindrical portion 40a and sealably engages the internal walls of neck 38b in the manner shown in FIG. 7. This prevents leakage of fluid from the pressurized container past the delivery spike and to the outside of the container.

Also forming a part of the delivery spike assembly of this form of the invention is a tubular conduit C that communicate with an external flow rate control means shown here as a cylindrical housing 65 having contained therewithin a porous mass of material 67 such as porous teflon, through which the discharging liquid must flow. Flow rate can be precisely controlled by proper selection of the material 67 in a manner well known to those skilled in the art.

Figure 6:
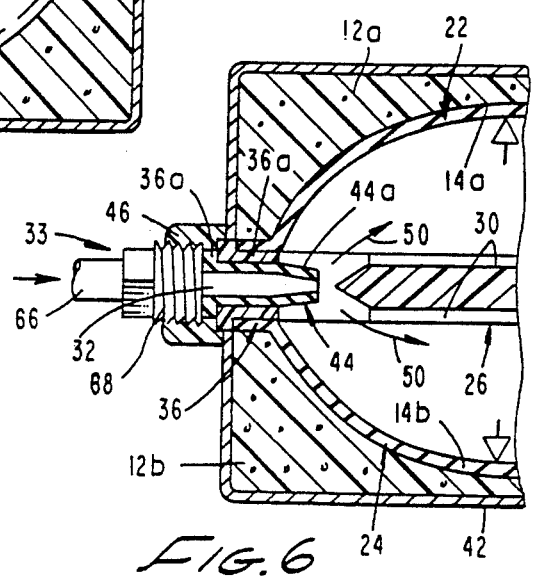
FIG. 6 is a fragmentary side-elevational, cross-sectional view of the fill port of the device.

In using the apparatus of the present invention, plug 48 is first removed and threadably inserted in its place is a fill tube 66 having a threaded fitting 68 which is receivable within retaining ring 46 (FIG. 6). In the aseptic filling process, the nutrient solution to be delivered to the patient is introduced through the check valve 44. The fluid being introduced will impinge upon membranes 22 and 24 causing them to distend from a first at rest position shown in FIGS. 4 and 5, wherein the central portions of the membranes are in proximity with support member 26, to a second distended position shown in FIGS. 6 and 7, wherein the central portions of the membranes are in proximity with the internal walls defining cavities 14a and 14b. Where permeable elastomeric membranes are used, gas in the solution being introduced into the carton can pass through the membranes 22 and 24 and migrate to porous foam blocks 12a and 12b with subsequent venting at time of use to atmosphere through orifices 38c. It is to be understood that distention of the membranes from the first to the second position creates internal stresses of predetermined direction and magnitude in the specifically tailored thin films of elastomeric membranes which tend to uniformly return them to their original, non-distended position shown in FIGS. 4 and 5.

So long as frangible diaphragm 56 is in tact, the beneficial agent or solution to be delivered to the patient will remain within the device. However, as soon as the diaphragm is ruptured by the delivery spike 40, the controllably stressed elastomeric membranes 22 and 24 will attempt to return to their original, non-distended configuration and will controllably and uniformly force the fluid outwardly through the delivery passageway 62 of the delivery spike into tube 63 and toward the patient in the direction of the arrow 64 shown in FIG. 7.

In certain applications, the retaining ring 46 and check valve assembly 44 can be recessed into body portions 12a and 12b so that after aseptic filling of the carton is complete, the outer most barrier of the encapsulation means can be folded over the check valve assembly in a manner to effectively seal it relative to atmosphere.

Referring now to FIGS. 10a, 11 and 12, another form of the liquid delivery apparatus of the present invention is there illustrated. This form of the invention is similar in most respects to the form of the invention described in the preceding paragraphs. Accordingly like numbers have been used to identify like components. The principal differences between this latter embodiment of the invention and the former embodiment resides in the provision of a differently configured check valve assembly 80 as well as differently configured distendable membrane assemblies 84.

The check valve assembly of this latter embodiment of the invention comprises an outer sleeve 86 which is receivable within fluid inlet 32. Provided proximate the outboard end of sleeve 86 is a flange 88 which is bondably interconnected with flange 36a of the inlet adapter 36. The check valve member of this alternate form of the invention comprises a generally cylindrically shaped member 90 having a body portion 92 and a reduced diameter neck portion 94. A shoulder 96 is formed at the junction of neck portion 94 and body portion 92. Check valve member 90 is reciprocally movable within sleeve 86 from an outward sealing position wherein shoulder 96 sealably engages an internal shoulder provided in member 88 to a retracted position wherein liquid will be permitted to flow through inlet port 32 and into pressural communication with the distendable membrane assemblies 84 of this form of the invention. It should be understood that once the device is pressurized by the filling of the nutritional fluids, the check valve member 90 will be urged into a sealing forward position blocking liquid flow outwardly through the inlet port 32. However, during the filling operation, the check valve member is movable rearwardly of sleeve 86 so as to permit fluid flow through a plurality of circumferentially spaced fluid flow passageways 97 provided in check valve member 90 (FIG. 11).

Turning now to FIG. 10a, it is to be noted that each of the distendable membranes of this later form of the invention comprises a laminate structure made up of a plurality of layers of elastomeric material 84a, 84b and 84c. This assemblage functions in much the same way as earlier described distendable membranes 22 and 24. However, by constructing each of the stored energy members from a composite of several distinct thin films or layers, the elastic characteristic of the stored energy means can be precisely tailored and can be uniquely constructed to function not only as a fluid driving medium but also as a gas permeability valve. The selective arrangement of the different films that make up the stored energy means, each with its own ascending permeability constant, will dictate the direction of flow of various gases and vapors. Vapors contained within the solution introduced into the device can pass through the stored energy means in one direction while external gases will be precluded from negative migration into the reservoir.

The solution contained within the device is delivered to the patient through the delivery spike assembly 40 in the same manner as was described in the discussion of the previous embodiment. Similarly, make-up air is supplied by the vent means through apertures 38(c) in the manner discussed in the preceding paragraphs.

Referring now to FIGS. 13, 14, 15 and 16, still another form of the liquid delivery apparatus of the present invention is there illustrated. This latest form of the invention is also similar in many respects to the invention described in the preceding paragraphs. Accordingly, like numbers are used in these figures to identify like components.

Figure 13:
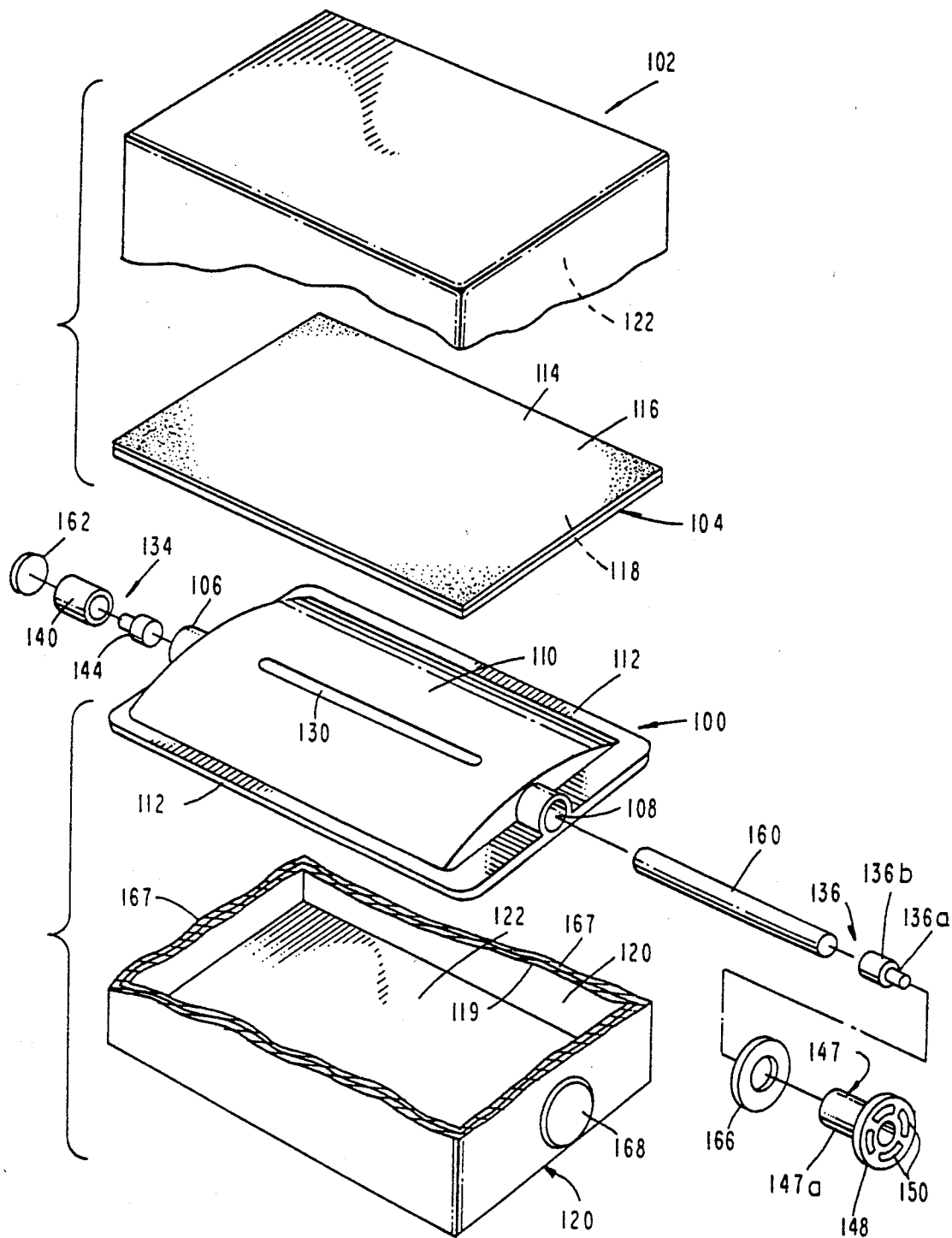
FIG. 13 is a generally perspective exploded view of another embodiment of the nutrient delivery apparatus of the invention.
Figure 20:
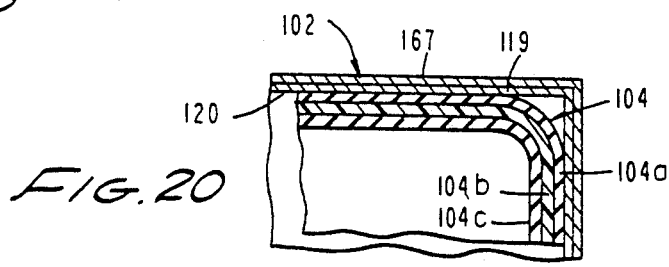
FIG. 20 is a fragmentary cross-sectional view of area 20—20 of FIG. 15.

As best seen by referring to FIG. 13, the liquid delivery apparatus of this latest form of the invention comprises a base assembly 100, a carton-like body 102 within which the base assembly is encapsulated and a distendable membrane assembly 104 which overlays base assembly 100. Base assembly 100 has a fluid inlet and a fluid outlet 106 and 108 respectively and includes a central, convex portion 110 which is circumscribed by an edge portion 112. Distendable membrane assembly 104 also includes a central portion 114 which is circumscribed by upper and lower edge portions 116 and 118 respectively. As shown in FIG. 20, distendable membrane assembly 104 can be made up of at least two, but preferably a plurality of thin film distendable membranes 104a, 104b and 104c. For example, layer 104a which is distal to the reservoir comprises a thin film elastomer of a first thickness and a first permeability. On the other hand, layer 104c which is proximal to the reservoir, comprises a thin elastomer film of a second thickness and a second permeability. This film is uniquely selected to be compatible in all respects with the fluid contined within the reservoir. Layer 104b can be of yet another thickness and permeability and, if desired can also have different perm-select characteristics. As previously described, the selective arrangement of the different films, each with its own individual permeability constants in ascending order, will dictate the direction of flow of selected gases and vapors through the stored energy means.

Figure 15:
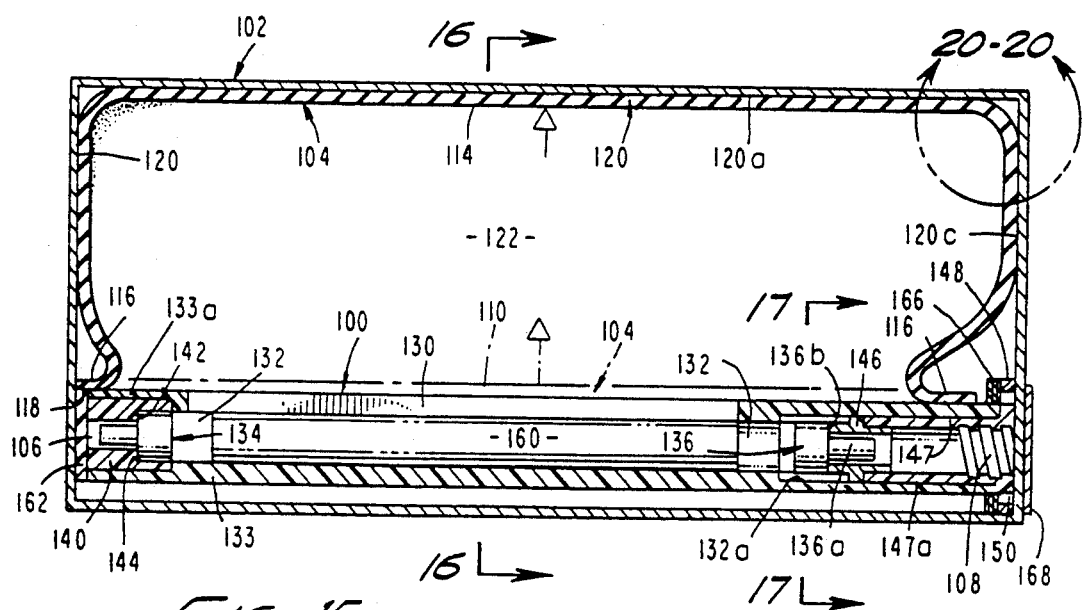
FIG. 15 is a cross-sectional view taken along lines 15—15 of FIG. 14.
Figure 16:
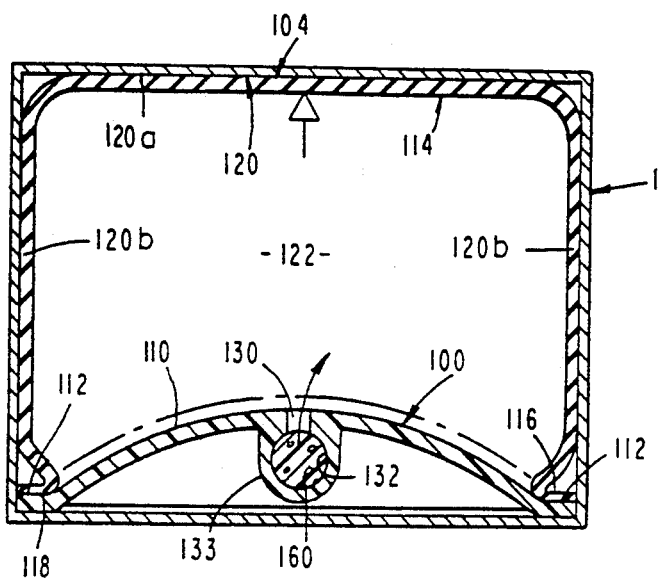
FIG. 16 is a cross-sectional view taken along lines 16—16 of FIG. 15.

Turning now to FIGS. 15, 16, and 20, it can be seen that body assembly 102 includes an inner barrier member 119 having internal surfaces 120 which define a cavity or fluid reservoir 122. Barrier member 119 is provided with end flaps (not shown) which can be folded over into the position shown in the drawings after the reservoir 122 is filled in the manner presently to be described. Distendable membrane assembly 104 is distendable from a first position wherein the central portion 114 thereof is in close proximity with the central portion 110 of base assembly 100 to a second distended position wherein central portion 114 is in close proximity with the upper internal walls 120a of body assembly or carton 102. The membrane assembly also moves into close proximity with the internal surfaces 120b of walls 120 of the carton (FIG. 16) and with the internal surfaces of end walls 120c (FIG. 15). As before, when the distendable membrane assembly 104 is distended from the first to the second position, internal stresses are developed within the membrane which tend to uniformly return it toward its first position in close proximity with the central portion 110 of base assembly 100.

Figure 14:
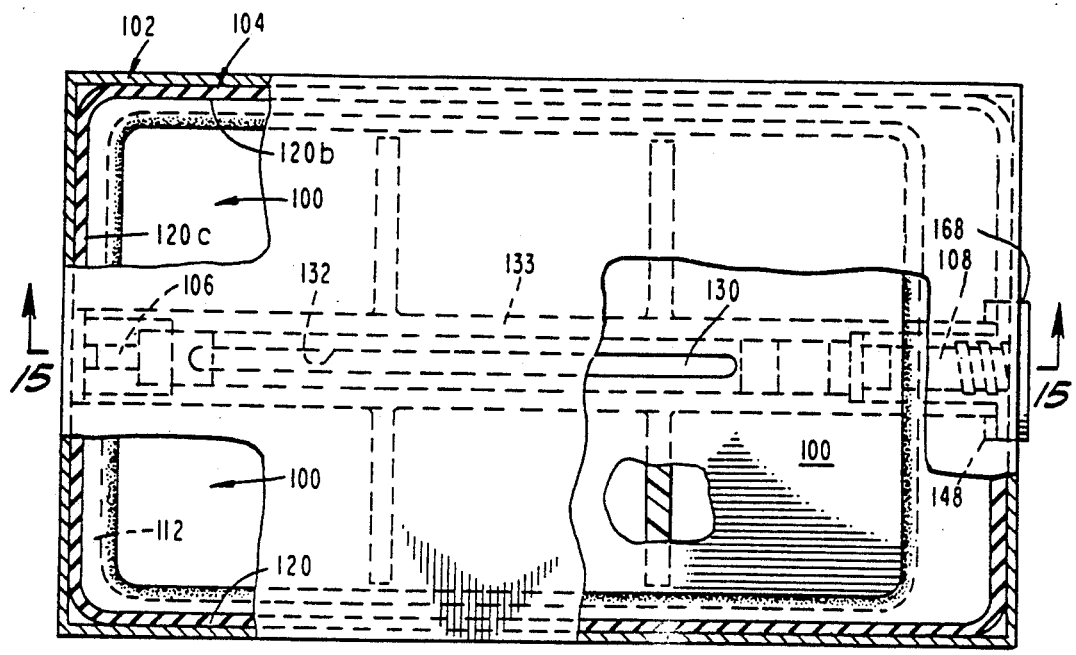
FIG. 14 is a plan view of the device partly broken away to show internal construction.

Referring to FIGS. 13, 14, and 16 it can be seen that base assembly 100 is provided with a longitudinally extending flow channel 130 which communicates with an internal longitudinally extending flow passageway 132 that extends between and interconnects together inlet 106 and outlet 108. As best seen in FIG. 16, flow passageway 132 is formed internally of a semitubular shaped, longitudinally extending protuberance 133 formed integrally with base assembly 100.

Disposed proximate the inlet portion of fluid passageway 132 is a check valve assembly generally designated by the numeral 134. A similar check valve 136 is disposed proximate the outlet portion of fluid passageway 132. Referring to FIG. 15, it can be seen that inlet check valve 134 is receivable within a cylindrically shaped retaining member 140 which is receivably within an enlarged diameter portion 133a of protuberance 133. Member 140 has an internal shoulder 142 adapted to engage an external shoulder 144 formed on check valve 134. When the check valve 134 is in the closed position shown in FIG. 15 wherein shoulder 144 is in engagement with internal shoulder 142 of member 140, the flow of fluid inwardly into fluid passageway 132 is blocked.

Check valve 136 which is positioned proximate the outlet of fluid passageway 132 is held in position within the fluid passageway by a retainer member 146 which is disposed within passageway 132 in engagement with an internally threaded outlet receptacle 147. Outlet receptacle 147 which comprises a part of the vent means of the invention, includes a tubular body portion 147a and flange portion 148 having a plurality of circumferentially spaced apertures 150 (FIG. 13). As best seen by referring to FIG. 15, the reduced diameter portion 136a of check valve 136 is movably receivable within a bore provided in retainer member 146. With the shoulder 136b of the check valve 136 in sealable engagement member 146 fluid flow through passageway 132 in a direction toward outlet 108 is effectively blocked.

Also disposed within fluid passageway 132, intermediate check valves 134 and 136, is a flow rate control means shown here as an elongated, generally cylindrically shaped porous filter member 160. Member 160 can be constructed of any inert porous material such as a ceramic or porous plactic, fluid permeable material and can be tailored to provide a precise rate of fluid flow through passageway 132 in a manner well known to those skilled in the art.

Figure 18:
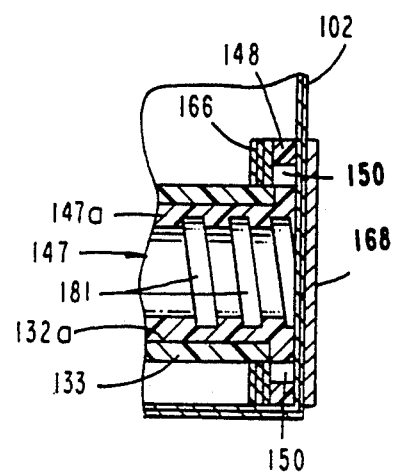
FIG. 18 is an enlarged fragmentary view of the outlet portion of the device.
Figure 17:
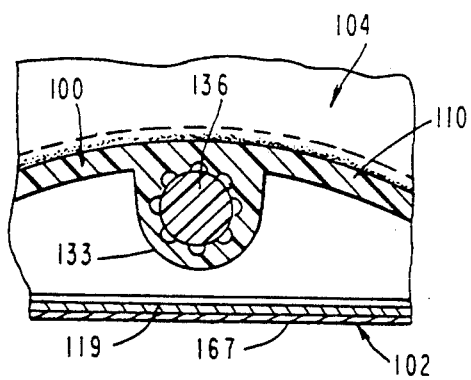
FIG. 17 is a cross-sectional view taken along lines 17—17 of FIG. 15.

As best seen in FIG. 18, at the outlet portion of the apparatus tubular body portion 147a of receptacle 147 is positioned within an enlarged diameter portion 132a of flow passageway 132 with flange 148 of member 147 positioned against base assembly 100. A hydrophobic filter vent means for venting air but not moisture is here shown as disk shaped member 166 which is appropriately bonded to the interior surfaces of flange 148 of member 147 in the manner shown in FIG. 18. A material such as hydrophobic PTFE, polytetrafluoroethylene incorporating laminated polypropylene or hydrophobic acrylic copolymer supported on nylon nonwoven substrates is suitable for the construction of member 166.

With outlet check valve 136 in a closed position, chamber or reservoir 122 is filled with the selected feeding solution by inserting an appropriate filling conduit into the inlet portion of the device (not shown). The filling conduit is adapted to move check valve 134 inwardly permitting the feeding solution to flow into passageway 132 and then outwardly of channel 130 where it impinges on membrane assembly 104 with sufficient pressure to distend it in to the position shown in FIGS. 15 and 16.

After reservoir 122 has been filled, the pressure of the solution within the reservoir will maintain both the inlet and outlet check valves 134 and 136 in the closed position shown in FIG. 15 Following filling of the reservoir, a retainer disk 162 is positioned over the inlet or filling port 106 and the end flaps of barrier member 119 and folded over to hold disk 162 as well as outlet receptacle 147 in position. This done, an outer barrier layer 167 (FIGS. 13 and 20) is emplaced over the entire assemblage so as to completely encapsulate it within a sealed oxygen impermeable, antimicrobial, leak-free aseptic container of the character previously described herein. Finally a disk shaped metalized seal 168 is positioned over the outer barrier in the proximity of the vent means or flange 148 of outlet receptacle 147. The apparatus of the invention is now ready for shipment storage and subsequent use in the field.

Figure 19:
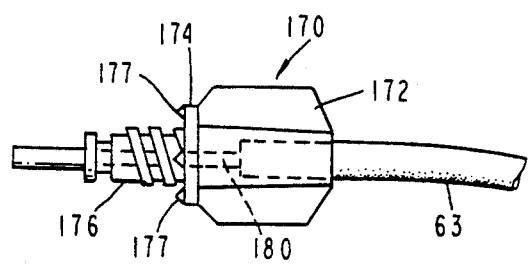
FIG. 19 is an enlarged fragmentary view of the delivery spike of this latest embodiment.

The feeding solution contained within reservoir 122 is accessed by a delivery spike 170 of a construction similar to delivery spike 140 of the earlier described embodiments. As shown in FIG. 19, delivery spike 170 comprises a finger grip portion 172, a flange portion 174 and an externally threaded neck portion 176. For a purpose presently to be described, a plurality of circumferentially spaced, outwardly extending pointed protuberances 177 are provided on flange portion 174.

Figure 21:
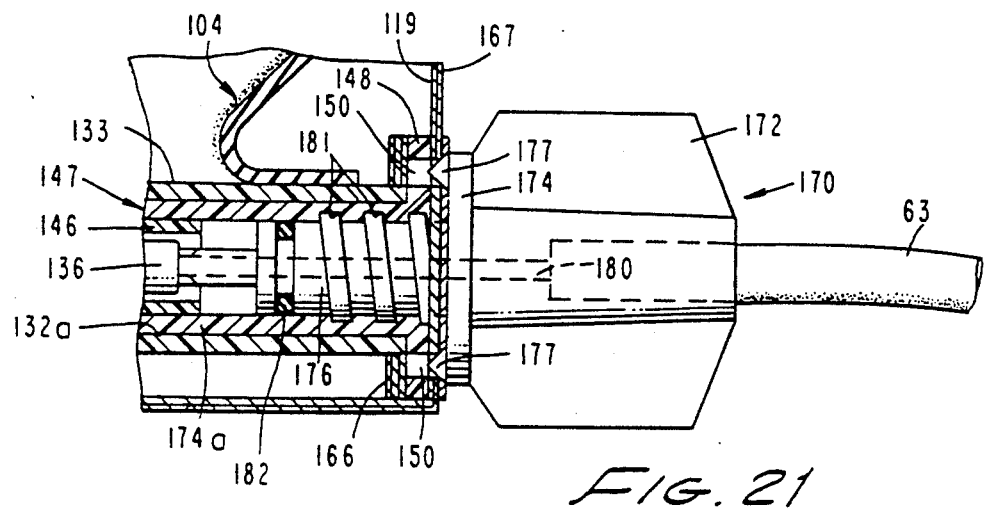
FIG. 21 is an enlarged fragmentary cross-sectional view of the delivery spike mated with the outlet port assembly of the device.

Turning now to FIG. 21, upon piercing the metalized seal 168 and the barrier layers 119 and 167, threads provided on neck portion 176 of the delivery spike can be moved into threadable engagement with the internal threads 181 provided on outlet receptacle 147 in the manner shown in FIG. 21. As the neck portion of the delivery spike advances into receptacle 147, the end of the neck portion will engage outlet check valve 136 moving it into an open position which will permit liquid within reservoir 122 to flow through channel 130, into passageway 132 and then into central passageway 180 provided in the delivery spike. As elastomeric O ring 182 is carried by neck portion 176 for engagement with the internal wall of the outlet receptacle to prevent leakage of the feeding solution past the delivery spike.

As illustrated in FIG. 21, as the check valve 136 is moved into the open position, protuberances 177 will pierce metalized seal 168 and will extend into vent apertures 150 thereby creating openings which permit make-up air to flow into the device as the feeding solution is introduced into the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:
1. A liquid delivery apparatus comprising:
 (a) a housing having internal walls defining a cavity;
 (b) a support disposed within said housing having a central portion, an edge portion circumscribing said central portion and including a liquid passage- way in communication with said cavity of said housing, said liquid passageway having an inlet and an outlet;

(c) a distendable membrane having a central portion circumscribed by an edge, said central portion spanning said central portion of said support with said edge being disposed in engagement with said edge portion of said support, said distendable membrane being distendable from a first position wherein said central portion is in close proximity with said support to a second position wherein said central portion is in close proximity of said internal walls defining said cavity, said distendable membrane in said second position having internal stresses tending to return it to said position, (d) means for sealably encapsulating said housing, said distendable membrane and said support, said means comprising an oxygen impermeable barrier surrounding said housing; said barrier comprising a structure made up of materials which cooperate to completely surround and encapsulate said housing in a manner to provide a substantially oxygen impermeable anti-microbial, leak-free aseptic container for containing the liquid to be delivered; and (e) means for permitting the flow of gases between atmosphere and said cavity of said housing as said distendable membrane moves from said second position to said first position.

2. A liquid delivery apparatus as defined in claim 1 further including flow rate control means disposed interiorly of said liquid passageway of said support for controlling the rate of low of fluid through said passageway.

3. A liquid delivery apparatus as defined in claim 1 further including a pair of porous bodies disposed interiorly of said cavity, each said body having internal walls defining a cavity, said support being disposed between said porous bodies.

4. A liquid delivery apparatus as defined in claim 3 further including a second distendable membrane having a central portion distendable from a first position in proximity with said support to a second position in proximity with said internal walls of one of said porous bodies.

5. An apparatus as defined in claim 4 in which distension of said second membrane from said first to said second position creates internal stresses tending to return said membrane to said first position.

6. An apparatus as defined in claim 5 in which said distendable membranes comprise multi-layers of elastic material.

7. An apparatus as defined in claim 6 further including check valve means disposed within said inlet of said support for permitting fluid flow in a first direction and for blocking fluid flow in a second direction.

8. An apparatus as defined in claim 7 further including a frangible diaphragm for closing said outlet of said support.

9. An apparatus as defined in claim 8 further including fluid delivery means having coupling means for interconnection with said outlet of said support and spike means for rupturing said frangible diaphragm upon interconnection of said coupling means with said outlet.

10. A liquid delivery apparatus comprising:

(a) a porous body, including first and second portions, each said portion comprising:

(i) internal walls defining a cavity, said cavity being circumscribed by an edge;

(ii) first and second spaced apart openings in communication with said cavity;

(b) a firs distendable membrane having a central portion circumscribed by an edge, said central portion spanning the cavity of said first body portion with said edge being disposed in engagement with said edge of said first body portion;

(c) a second distendable membrane having a central portion circumscribed by an edge, said central portion spanning the cavity in said second body portion with said edge being disposed in engagement with said edge of said second body portion;

(d) a fluid inlet port disposed within said first opening in said body portion;

(e) a fluid outlet port disposed within said second opening in said body portions;

(f) a support member disposed intermediate said first and second distendable membranes, said support member having a fluid passageway in communication with said fluid inlet and outlet ports;

(g) liquid delivery means in communication with said fluid outlet port for delivering fluid from said apparatus; and (h) encapsulating means for sealably encapsulating said body, said encapsulating means comprising a laminate structure made up of at least two layers of materials which cooperate to completely surround and encapsulate said housing in a manner to provide a substantially oxygen impermeable anti-microbial, leak-free aseptic container for containing the liquid to be delivered.

11. An apparatus as defined in claim 10 in which said liquid delivery means includes flow control means disposed externally of said encapsulating means for controlling the rate of liquid flow to the patient and in which said fluid outlet port includes vent means for venting gases from said cavities to atmosphere.

12. An apparatus as defined in claim 11 in which said first and second distendable membranes are distendable from a first position wherein said central portions of said membranes are in proximity with said support member to a second position wherein said central portions of said membranes are in proximity with said internal walls defining said cavities in said first and second body portions.

13. An apparatus as defined in claim 11 in which distension of said membranes from said first to said second position creates internal stresses tending to return said membranes to said first position.

14. An apparatus as defined in claim 11 in which said distendable membranes each comprise multi-layers of elastic material.

15. An apparatus as defined in claim 11, further including check valve means disposed within said fluid inlet port for permitting fluid flow in a first direction and for blocking fluid flow in a second direction.

16. An apparatus as defined in claim 11, further including a frangible diaphragm for closing said fluid outlet port.

17. An apparatus as defined in claim 16 in which said fluid delivery means includes coupling means for interconnection with said fluid outlet port and spike means for rupturing said frangible diaphragm upon interconnection of said coupling means with said fluid outlet.

18. An apparatus as defined in claim 17, further including closure means for closing said vent means.

19. An apparatus for enteral feeding of a patient comprising:
(a) a housing having internal walls defining a cavity;
(b) a porous body disposed within said housing, said body including first and second portions, each said portion comprising:
  (i) internal walls defining a cavity, said cavity being circumscribed by an edge;
  (ii) first and second spaced apart openings in communication with said cavity;
(c) a first distendable membrane assembly comprising a plurality of thin films, said assembly having a central portion circumscribed by an edge, said central portion spanning the cavity of said first body portion with said edge being disposed in engagement with said edge of said first body portion,
(d) a second distendable membrane assembly comprising a plurality of thin films, said assembly having a central potion spanning the cavity in said second body portion with said edge being disposed in engagement with said edge of said second body portion;
(e) a fluid inlet port disposed within said first opening in said body portions;
(f) a fluid outlet port disposed within said second opening in said body portions;
(g) a support member disposed intermediate said first and second distendable membrane assemblies, said support member having a fluid passageway in communication with said first and second membrane assemblies and with said fluid inlet and outlet ports;
(h) liquid delivery means in communication with said fluid outlet port for delivering fluid to a patient; and
(i) encapsulating means for sealably encapsulating said body, said encapsulating means comprising an outer paper wrap covering an inner metalized wrap which cooperate to completely surround and encapsulate said housing in a manner to provide a substantially oxygen impermeable anti-microbial, leak-free aseptic container for containing the liquid to be delivered.

20. An apparats as defined in claim 19 in which said fluid outlet port includes vent means for venting gases from said cavities to atmosphere.

* * * * *